(12) United States Patent
Bardowski et al.

(10) Patent No.: US 7,417,135 B2
(45) Date of Patent: Aug. 26, 2008

(54) PLASMIDIC GENE, WAYS OF ACQUIRING THIS GENE, THE AMYLOLYTIC ENZYME IT ENCODES AND ITS APPLICATION

(76) Inventors: Jacek Bardowski, ul. Zythia 55/9, Warsaw (PL) PL-01-179; Monika Doman, ul. 15 PP "Wilkow" 2/9, Pulawy (PL) PL 24-100; Zdzislaw Targonski, ul. Bazylianowka 5, Lublin (PL) 20-144; Adam Wasko, ul. Utanow 7/17, Lublin (PL) 20-554; Pierre Renault, 9, rue Magellan, Monligny-le-Bretonneux (FR) F-78180; Jamila Mondoloni, 3, Rue des Neteides, Montigny-le-Bretonneux (FR) F-78180

( * ) Notice: Subject to any disclaimer, the term of this patent is extended or adjusted under 35 U.S.C. 154(b) by 289 days.

(21) Appl. No.: 10/488,645

(22) PCT Filed: Jun. 26, 2002

(86) PCT No.: PCT/PL02/00041

§ 371 (c)(1),
(2), (4) Date: Oct. 12, 2004

(87) PCT Pub. No.: WO03/008587

PCT Pub. Date: Jan. 30, 2003

(65) Prior Publication Data

US 2005/0064574 A1    Mar. 24, 2005

(30) Foreign Application Priority Data

Jul. 19, 2001  (PL) ..................................... 348789

(51) Int. Cl.
*C07H 21/04* (2006.01)
*A61K 38/00* (2006.01)
*C12N 1/20* (2006.01)
*C12N 1/00* (2006.01)
*C12N 9/00* (2006.01)
*C12P 21/06* (2006.01)
*C12P 21/04* (2006.01)
*G01N 33/00* (2006.01)

(52) U.S. Cl. .................. 536/23.7; 530/300; 435/252.31; 435/243; 435/68.1; 435/71.1; 435/183; 436/86

(58) Field of Classification Search ................. 530/300; 536/23.1, 23.7; 435/252.31, 243, 66.1, 71.1, 435/183, 68.1; 436/86
See application file for complete search history.

(56) References Cited

FOREIGN PATENT DOCUMENTS

EP    0311469    4/1989
PL    189090    * 12/1999

OTHER PUBLICATIONS

Translation of Abstract Bardowski 326573 (PL 189090).*
Journal of Biological Chemistry, vol. 268, No. 22, 1993, pp. 16332-16344 article entitled "Sequencing of the amylopullulanase (apu) gene of Thermoanaerabacter ethanolicus 39E, and identification of the active site by site-directed mutagenesis." author Saroj P. Mathupapa et al.
Applied And Environmental Microbiology, vol. 63, No. 10, 1997, pp. 3752-3756, article entitled "Isolation and overexpression of a gene encoding an extracellular beta—(1, 3-1, 4)—glucanase from *Streptococcus bovis* JB1." author, Sait M. Ekinci et al.
International Search Report PCT/PL02/00041 dated Jul. 17, 2003.

* cited by examiner

*Primary Examiner*—Robert A Zeman
*Assistant Examiner*—Lakia J Tongue
(74) *Attorney, Agent, or Firm*—Rader, Fishman & Grauer, PLLC; James F. Kamp (57) ABSTRACT

The object of the invention is a novel plasmidic gene encoding an amylolytic enzyme which after introduction into a microbial strain, favorably bacterial, especially *Lactococcus lactis*, enables the production of the encoded amylolytic enzyme, the ways of acquiring this gene and the industrial application of the enzyme it encodes.

Figure 1:
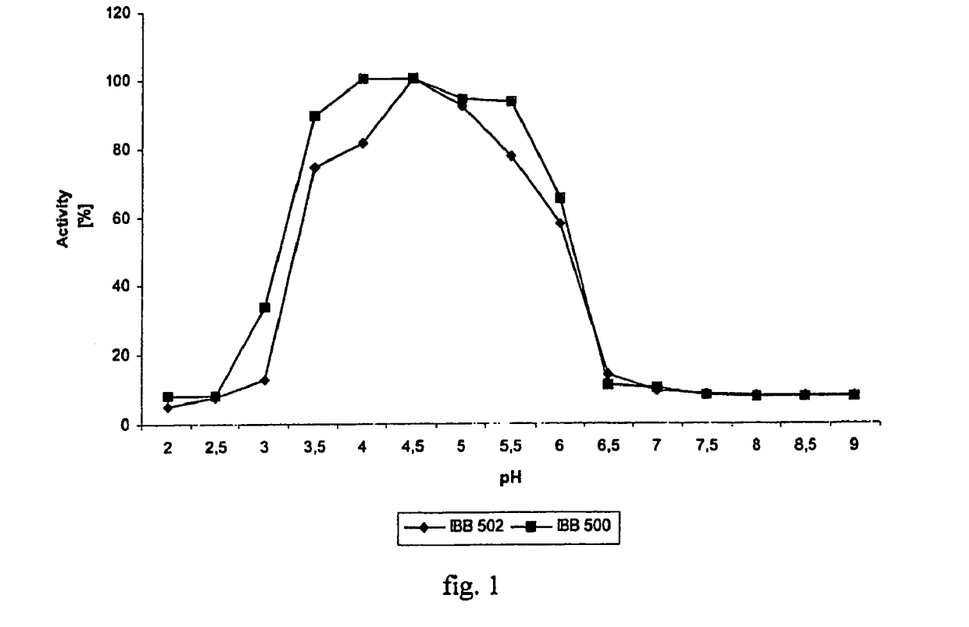
Figure 2:
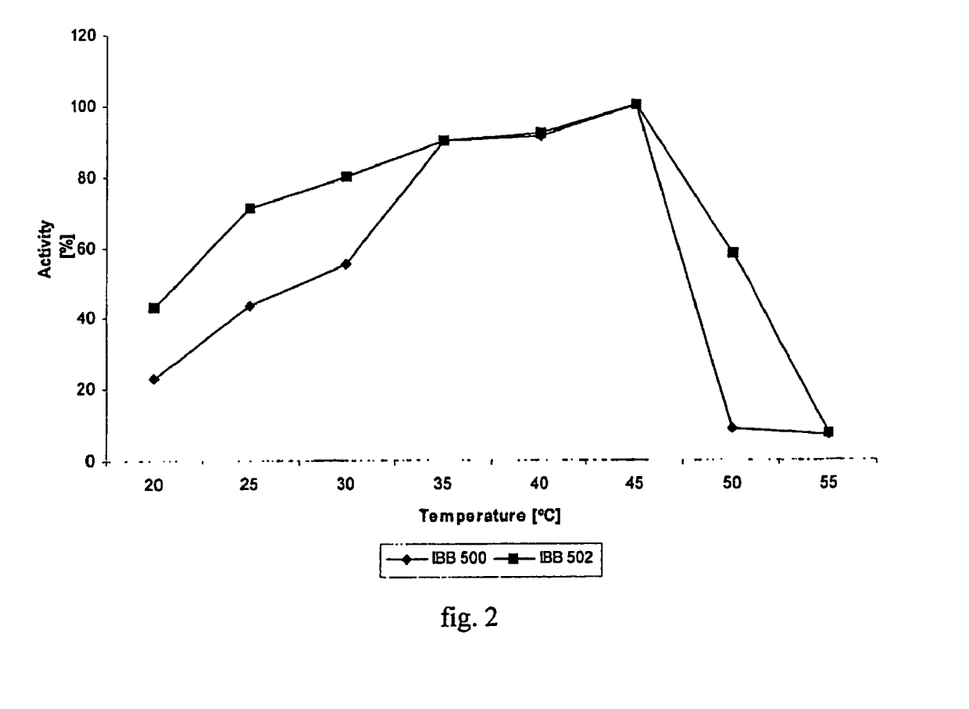
Figure 3:
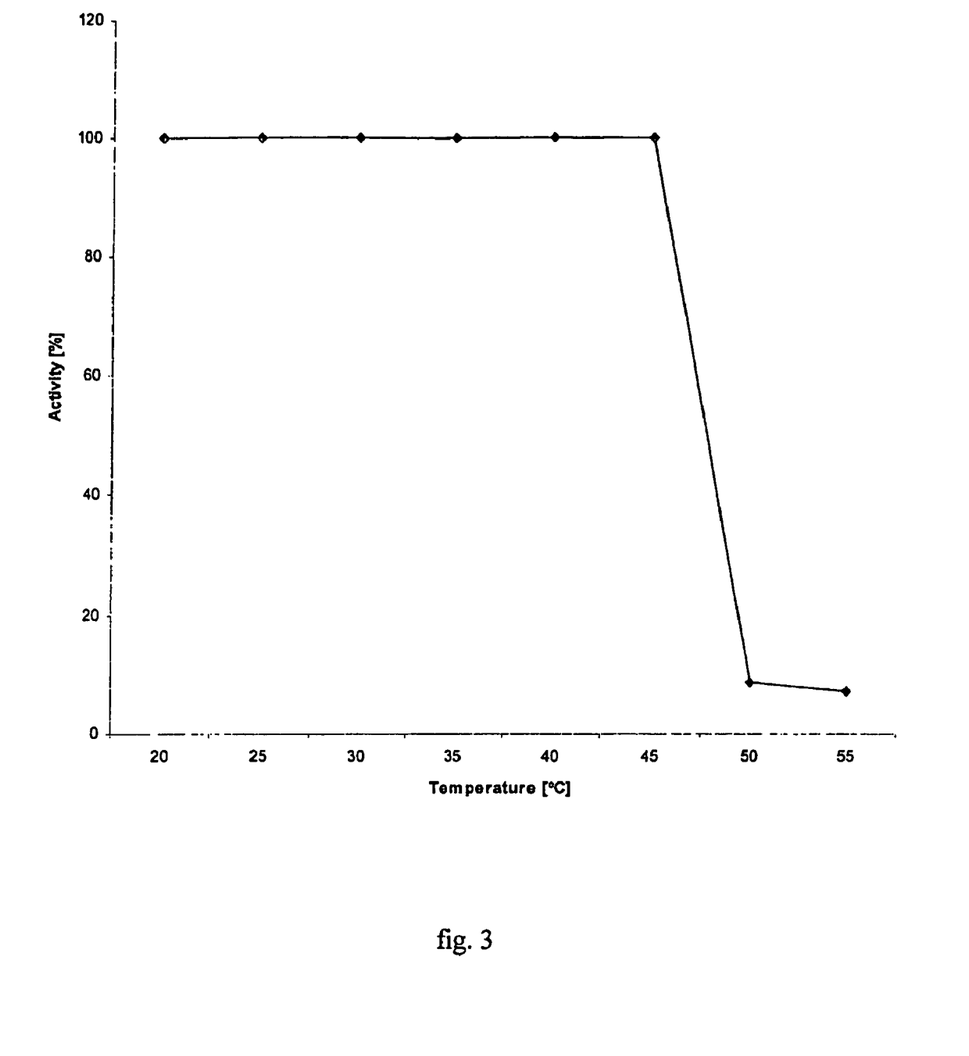

2 Claims, 2 Drawing Sheets fig. 1 fig. 2 fig. 3

PLASMIDIC GENE, WAYS OF ACQUIRING THIS GENE, THE AMYLOLYTIC ENZYME IT ENCODES AND ITS APPLICATION

BACKGROUND OF THE INVENTION

Lactic acid bacteria are capable of utilizing many different sugars as a source of carbon and energy (De Vos W. 1996. Antonie van Leeuwenhoek 70: 223). In a significant majority these sugars are monosaccharides or disaccharides. The ability of lactic acid bacteria to catabolize carbohydrates is widely used in biotechnological processes linked with food production (Libudzisz Z., Walczak P. and Bardowski J. (ed.), 1998. Lactic Acid Bacteria—classification, metabolism, genetics, application. (In polish) Monographies, Lódź; Aleksandrzak T., Kowalczyk M., Kok J., Bardowski J. 2000, Food Biotechnol. 17: 61, Elsevier Science B.V., Amsterdam). One of these processes is the production of fermented milk products. The main sugar in milk is lactose, which catabolism is a feature rather commonly present among lactic acid bacteria (Bardowski J. 1995. Przeglad Mleczarski 11: 315; Van Rooijen R. J. 1992. Lactose catabolism in *Lactococcus lactis*. Ph.D thesis, Wageningen, The Netherlands).

Yet another natural source, besides milk, of food production are plants. These biotechnological processes are frequently conducted with the use of lactic acid bacteria. However, in plant material, differently than in milk, polysaccharides such as cellobiose or starch are present. Thus, in the microbial conversion of plant material these microbials are incorporated which have either cellulolytic or amylolytic abilities. Lactic acid bacteria lack the ability to degrade cellulose.

However, the ability to degrade starch is, in this group of bacteria, a feature limited basically to a few strains of the *Lactobacillus* genus (cit. after Giraud E., A. Chapailler and M. Raimbault. 1994. Appl. Environ. Microbiol. 60: 4319). Some of these bacteria, belonging to the *L. plantarum, L. amylophilus*, or *L. amylovorus* species produce α-amylase (Fitzsimons A. and O'Connell. 1994. FEMS Microbiol. Letts. 116:137; Pompeyo C C., Gomez M S., Gasparian S., J. Morlon-Guyot 1993. Appl. Microbiol. Biotechnol. 40: 266).

It has been determined that besides strains from *Lactobacillus* genus, some strains of *Lactococcus* genus, naturally existing in the environment, also demonstrate this ability since strains which degrade starch were found among *Lactococcus* strains isolated from natural habitats (Domań M., E. Czerniec, Z. Targoński and J. Bardowski. (2000), Food Biotechnology 17:67, Elsevier Science B.V., Amsterdam).

Unexpectedly, it has been discovered that also other strains, especially from the *Lactococcus lactis* species, after introducing a specific gene structure according to the invention, are capable of producing a novel amylolytic enzyme which is encoded by this gene and which is secreted into the environment.

SUMMARY OF THE INVENTION

This invention is directed to a novel plasmidic gene encoding an amylolytic enzyme which after introduction into a microbial strain, favorably bacterial, especially *Lactococcus lactis*, enables the production of the encoded amylolytic enzyme, as well as ways of obtaining this gene and the industrial application of the enzyme it encodes.

DESCRIPTION OF THE PREFERRED EMBODIMENTS

The novel plasmidic gene encoding the novel amylolytic enzyme secreted into the environment, according to the invention has the following nucleotide sequence (top strand: SEQ. ID NO. 1 and bottom strand: SEQ. ID NO. 2):

```
     5'
         ATGAAAAAAACAAAATTAAGAATTTGTCTTTTCCCAATCGTACTGCTTATCAGTTTTACA
       1 ---+---------+---------+---------+---------+---------+------    60
         TACTTTTTTTGTTTTAATTCTTAAACAGAAAAGGGTTAGCATGACGAATAGTCAAAATGT

TTGCTATCCAATGGAACTGGTAAACAGATTGTTTTTGCTACATCTTCATCAGAATATGCT
      61 ---+---------+---------+---------+---------+---------+------   120
         AACGATAGGTTACCTTGACCATTTGTCTAACAAAAACGATGTAGAAGTAGTCTTATACGA

ACACAAGCTCTGTCTGACGAGAAAAATGCCACACAAAACAATGATTTTACATCTTTTGAT
     121 ---+---------+---------+---------+---------+---------+------   180
         TGTGTTCGAGACAGACTGCTCTTTTTACGGTGTGTTTTGTTACTAAAATGTAGAAAACTA

ATAAATGGGCCTATGAAGGGACAGATTTGGGATTTAACTATTCAACAACCAGTACTACT
     181 ---+---------+---------+---------+---------+---------+------   240
         TATTTTACCCGGATACTTCCCTGTCTAAACCCTAAATTGATAAGTTGTTGGTCATGATGA

TTCAAAATCTGGTCACCAACTGCGACGAGCGTGCAGCTGATAAGTTATGGGACGAATACC
     241 ---+---------+---------+---------+---------+---------+------   300
         AAGTTTTAGACCAGTGGTTCACGCTGCTCGCACGTCGACTATTCAATACCCTGCTTATGG

AATCCGACAGCGGCACAGGTCTCAGCGAAAGCAATGACACGCGGGACATCAGCGACACCA
     301 ---+---------+---------+---------+---------+---------+------   360
         TTAGGCTGTCGCCGTGTCCAGAGTCGCTTTCGTTACTGTGCGCCCTGTAGTCGCTGTGGT

ACTAATCACGCAACCAATACGATTGGGGTGTGGACTTTGACCGTTCCTGGCAATCAAAAT
     361 ---+---------+---------+---------+---------+---------+------   420
         TGATTAGTGCGTTGGTTATGCTAACCCCACACCTGAAACTGGCAAGGACCGTTAGTTTTA

GGCATGGTTTATGCTTACAAACTAACTTTTGCTGACGGAACCGTTAGTGATTATGCTGGG
     421 ---+---------+---------+---------+---------+---------+------   480
         CCGTACCAAATACCAATGTTTGATTGAAAACGACTGCCTTGGCAATCACTAATACGACCC
```

-continued

```
     TCAACTTATGGAACACTTTCTACAAGTTCTGTCAGCAATACAACCAATGATCCTTATTCT
481  ---+---------+---------+---------+---------+---------+------  540
     AGTTGAATACCTTGTGAAAGATGTTCAAGACAGTCGTTATGTTGGTTACTAGGAATAAGA

ATTGCGACGACACAAGGTGGAAATCGTTCAGTTGTCGAATCGTCTGCAAACCTCGCGTCA
541  ---+---------+---------+---------+---------+---------+------  600
     TAACGCTGCTGTGTTCCACCTTTAGCAAGTCAACAGCTTAGCAGACGTTTGGAGCGCAGT

AATCTGGCACTTGCGCAAGGCAAATCTGCAACTTGGCGGGTAGCAAGTCCAACACAAGCC
601  ---+---------+---------+---------+---------+---------+------  660
     TTAGACCGTGAACGCGTTCCGTTTAGACGTTGAACCCCCCATCGTTCAGCTTGTGTTCGG

ATCGTTGACGAACTACATATTCGTGATTTTACAAGCTCATCAACATCTGGTGTTTCGGCT
661  ---+---------+---------+---------+---------+---------+------  720
     TAGCAACTGCTTGATGTATAAGCACTAAAATGTTCGAGTAGTTGTAGACCACAAAGCCGA

GGTAATCGTGGTAAGTTTCTCGGAGTGATTCAGTCAGGAACAACTGATCCAAATACAGGT
721  ---+---------+---------+---------+---------+---------+------  780
     CCATTAGCACCATTCAAAGAGCCTCACTAAGTCAGTCCTTGTTGACTAGGTTTATGTCCA

ACAGCGACTGGACTTGATTATCTGAAAAACGAGGGTTTTAACTACATTCAACTTCATGCC
781  ---+---------+---------+---------+---------+---------+------  840
     TGTCGCTGACCTGAACTAATAGACTTTTTGCTCCCAAAATTGATGTAAGTTGAAGTACGG

AGCCAGTCAGTATGCGTCGGTCAACGAAGCCGGAACCGTACTACTGCGCAACCGAATAAC
841  ---+---------+---------+---------+---------+---------+------  900
     TCGGTCAGTCATACGCAGCCAGTTGCTTCGCCCTTGGCATGATGACGCGTTGGCTTATTG

TTCAACTGGGGATATGACCCACAAATGAAATGGTACCAGAGCGAATATGCCAGTAATTCT
901  ---+---------+---------+---------+---------+---------+------  960
     AAGTTGACCCCTATACTGGGTGTTTACTTTACCATGGTCTCGCTTATACGGTCATTAAGA

GTCAATCCTGTCACACGTATTAATGAAATGAAAGAAATGGTACAAGGCTTGCATACAAAT
961  ---+---------+---------+---------+---------+---------+------  1020
     CAGTTAGGACAGTGTGCATAATTACTTTACTTTCTTTACCATGTTCCGAACGTATGTTTA

GGGATTAGCGTGGTAATGGATATGGTTCTCAATCACGTCTATAGTCAGTCAGCATCCGCT
1021 ---+---------+---------+---------+---------+---------+------  1080
     CCCTAATCGCACCATTACCTATACCAAGAGTTAGTGCAGATATCAGTCAGTCGTAGGCGA

TTTGAAAAGCCGAGCCGGGCTATTATTTCCGCAAAAATACGCAATCTGGGTGTGGCAAT
1081 ---+---------+---------+---------+---------+---------+------  1140
     AAACTTTTTCGGCTCGGCCCGATAATAAAGGCGTTTTTATGCGTTAGACCCACACCGTTA

GATACGGCGAGCAACCACGAAATGTTTGGTAAATACATTATTGACTCTGTCACTTACTGG
1141 ---+---------+---------+---------+---------+---------+------  1200
     CTATGCCGCTCGTTGGTGCTTTACAAACCATTTATGTAATAACTGAGACAGTGAATGACC

GCGAAAAATTATGATATTGACGGCTTCCGTTTTGATGAAATGACACTTTTAGACAGCACG
1201 ---+---------+---------+---------+---------+---------+------  1260
     CGCTTTTTAATACTATAACTGCCGAAGGCAAAACTACTTTACTGTGAAAATCTGTCGTGC

ACTATGAATAAACTGCGTGCCGCACTGACAGCACTTGACCCACATATTATCATGTATGGC
1261 ---+---------+---------+---------+---------+---------+------  1320
     TGATACTTATTTGACGCACGGCGTGACTGTCGTGAACTGGGTGTATAATAGTACATACCG

GAAGGTTGGGGCGATTCTAATGCAAATAATATTCCTGAAACGTCTATCAATAATTACAAA
1321 ---+---------+---------+---------+---------+---------+------  1380
     CTTCCAACCCCGCTAAGATTACGTTTATTATAAGGACTTTGCAGATAGTTATTAATGTTT

AATGTTCCTGGTATTGGTTTTTTCAATCCTGGTGAACGTGACGCCATCAGTAATAATGGA
1381 ---+---------+---------+---------+---------+---------+------  1440
     TTACAAGGACCATAACCAAAAAGTTAGGACCACTTGCACTGCGGTAGTCATTATTACCT

GGTTCTGCAGGTGGATTCGCAGCAGGAAATACGGCAAGTACTATAACGGTCGCAGGAGCA
1441 ---+---------+---------+---------+---------+---------+------  1500
     CCAAGACGTCCACCTAAGCGTCGTCCTTTATGCCGTTCATGATATTGCCAGCGTCCTCGT

CTTTTGGCTTCTGCAGGTTGGAACGGAAATGGCACAGTGCAAGCTTTTTTGACGCCAAGC
1501 ---+---------+---------+---------+---------+---------+------  1560
     GAAAACCGAAGACCTCCAACCTTGCCTTTACCGTGTCACGTTCGAAAAAACTGCGGTTCG

CAGTCTATCAATTATGTTGAATGTCATGATAGCTTCACCTTAAATGACTCACTCTGGTCA
1561 ---+---------+---------+---------+---------+---------+------  1620
     GTCAGATAGTTAATACAACTTACAGTACTATCGAAGTGGAATTTACTGAGTGAGACCAGT

GCTGATCCGAATGATTCTGTGGCGACACATCAAGCGCGAGTGACGCTCGCAAATGCCACG
1621 ---+---------+---------+---------+---------+---------+------  1680
     CGACTAGGCTTACTAAGACACCGCTGTGTAGTTCGCGCTCACTGCGAGCGTTTACGGTGC
```

```
                    -continued
       AATATTCTTGCAAACGGTGTGACATTTATGGAAACAGGACAGGAGTTTGACCAGTCCAAA
1681   ---+---------+---------+---------+---------+---------+------  1740
       TTATAAGAACGTTTGCCACACTGTAAATACCTTTGTCCTGTCCTCAAACTGGTCAGGTTT TTAGTCAATCCGTCAAATCTGACGCCGCTCTCCCCTACACAGACACAGGCTTATCAATCG
1741   ---+---------+---------+---------+---------+---------+------  1800
       AATCAGTTAGGCAGTTTAGACTGCGGCGAGAGGGGATGTGTCTGTGTCCGAATAGTTAGC GGTAGTATGGAAAAACCTGCATGGTATCCTGCGTCATGGGATACTGCCAAAAATTCATAC
1801   ---+---------+---------+---------+---------+---------+------  1860
       CCATCATACCTTTTTGGACGTACCATAGGACGCAGTACCCTATGACGGTTTTTAAGTATG AATGGACTTTTTGGCTTGGCTAGTAATGGTACTTACTATGGCAATTATTGGCCAGGAAGT
1861   ---+---------+---------+---------+---------+---------+------  1920
       TTACCTGAAAAACCGAACCGATCATTACCATGAATGATACCGTTAATAACCGGTCCTTCA AATCTCTACACCCCAGTAGTTGCGGGGATGTAGTCAATGCCATGAATTGGGATAATGTC
1921   ---+---------+---------+---------+---------+---------+------  1980
       TTAGAGATGTGGGGTCATCAACGCCCCCTACATCAGTTACGGTACTTAACCCTATTACAG AAGGACAATCAAAATGCTGTTAATTTTATTGGAAATTTGATGAAATTTAAAAAATCCAAT
1981   ---+---------+---------+---------+---------+---------+------  2040
       TTCCTGTTAGTTTTACGACAATTAAAATAACCTTTAAACTACTTTAAATTTTTTAGGTTA CCGCAATTTTGGCCTGATGATTATAGCAAACTTGCTTGGACTCCTACCAGTATAGGTGTA
2041   ---+---------+---------+---------+---------+---------+------  2100
       GGCGTTAAAACCGGACTACTAATATCGTTTGAACGAACCTGAGGATGGTCATATCCACAT GAAAATGTCACAAATGCGTCAAACGGAGTGATCACAGAAGAATTAACATCGGGTGCGACC
2101   ---+---------+---------+---------+---------+---------+------  2160
       CTTTTACAGTGTTTACGCAGTTTGCCTCACTAGTGTCTTCTTAATTGTAGCCCACGCTGG AAATATTTAGTCATATTGAATGCTAGCGGTAATTCGGTCAAAATTGGTCAAGGTGGTCAG
2161   ---+---------+---------+---------+---------+---------+------  2220
       TTTATAAATCAGTATAACTTACGATCGCCATTAAGCCAGTTTTAACCAGTTCCACCAGTC TTTTATGGGGTGTCAAATTTGACAGGTAAAACTGTGATAATTTCTGACGATAGTAGCTTA
2221   ---+---------+---------+---------+---------+---------+------  2280
       AAAATACCCCACAGTTTAAACTGTCCATTTTGACACTATTAAAGACTGCTATCATCGAAT ACAGCTAATCAAGTTTTGAATAGCTCTGTCACTCTGTCAAATTTGACAGTCACCGTTATC
2281   ---+---------+---------+---------+---------+---------+------  2340
       TGTCGATTAGTTCAAAACTTATCGAGACAGTGAGACAGTTTAAACTGTCAGTGGCAATAG CAACTTTCTAAATAA
2341   ---+----------+-  2355              3'
       GTTGAAAGATTTATT
```

The novel gene according to the invention favorably has at its 5' end an additional nucleotide sequence which together give the following nucleotide structure: (top strand: SEQ. ID NO. 3 and bottom strand: SEQ. ID NO. 4)

```
     TTACGTTAGCTGGAGAATCCACCGTGTGGAGCCTCCGTCTCACGGTTGCTCCGTGTTACG
1    ---------+---------+---------+---------+---------+---------+  60
     AATGCAATCGACCTCTTAGGTGGCACACCTCGGAGGCAGAGTGCCAACGAGGCACAATGC

GTAATTCCGCTGCTATAAAGTAATAACTAATAACAAATTAAATAGCAGTATAAAATTTTG
61   ---------+---------+---------+---------+---------+---------+  120
     CATTAAGGCGACGATATTTCATTATTGATTATTGTTTAATTTATCGTCATATTTTAAAAC

ATAATTTGAAGATTATTTTAATATTTACCTGAATAACACTTTAGAAAACTGAAATATCTA
121  ---------+---------+---------+---------+---------+---------+  180
     TATTAAACTTCTAATAAAATTATAAATGGACTTATTGTGAAATCTTTTGACTTTATAGAT

TAACTCCAGATCAATAGTGGAAATACGTACAATTTGATATAAGAGATTTTTGTATCAAAA
181  ---------+---------+---------+---------+---------+---------+  240
     ATTGAGGTCTAGTTATCACCTTTATGCATGTTAAACTATATTCTCTAAAAACATAGTTTT

AAAATTTTTTAAACAAAATGCACTAAAAGATTTTTTTGTGTTGCTGAGAGGTTGCAAAA
241  ---------+---------+---------+---------+---------+---------+  300
     TTTTAAAAAATTTGTTTTACGTGATTTTCTAAAAAAACACAACGACTCTCCAACGTTTT

TGATACCGCAAGGTATATAATGGTTACGTAATTAGTGCAAGCGCTTGCATTTTTTGTGAA
301  ---------+---------+---------+---------+---------+---------+  360
     ACTATGGCGTTCCATATATTACCAATGCATTAATCACGTTCGCGAACGTAAAAACACTT
```

```
                  -continued
       AAAAGTCCTTTTATTTATTTATCTTATTGCTTTGAAAGATATTGTTAAAAATAAATAAAA
  361  ---------+---------+---------+---------+---------+---------+  420
       TTTTCAGGAAAATAAATAAATAGAATAACGAAACTTTCTATAACAATTTTTATTTATTTT TCGTTATAAACTCAATATAATAAGGAGAGCTAAATAATGAAAAAAACAAAATTAAGAATT
  421  ---------+---------+---------+---------+---------+---------+  480
       AGCAATATTTGAGTTATATTATTCCTCTCGATTTATTACTTTTTTTGTTTTAATTCTTAA TGTCTTTTCCCAATCGTACTGCTTATCAGTTTTACATTGCTATCCAATGGAACTGGTAAA
  481  ---------+---------+---------+---------+---------+---------+  540
       ACAGAAAAGGGTTAGCATGACGAATAGTCAAAATGTAACGATAGGTTACCTTGACCATTT CAGATTGTTTTGCTACATCTTCATCAGAATATGCTACACAAGCTCTGTCTGACGAGAAA
  541  ---------+---------+---------+---------+---------+---------+  600
       GTCTAACAAAAACGATGTAGAAGTAGTCTTATACGATGTGTTCGAGACAGACTGCTCTTT AATGCCACACAAAACAATGATTTTACATCTTTTGATATAAAATGGGCCTATGAAGGGACA
  601  ---------+---------+---------+---------+---------+---------+  660
       TTACGGTGTGTTTTGTTACTAAAATGTAGAAAACTATATTTTACCCGGATACTTCCCTGT GATTTGGGATTTAACTATTCAACAACCAGTACTACTTTCAAAATCTGGTCACCAACTGCG
  661  ---------+---------+---------+---------+---------+---------+  720
       CTAAACCCTAAATTGATAAGTTGTTGGTCATGATGAAAGTTTTAGACCAGTGGTTGACGC ACGAGCGTGCAGCTGATAAGTTATGGGACGAATACCAATCCGACAGCGGCACAGGTCTCA
  721  ---------+---------+---------+---------+---------+---------+  780
       TGCTCGCACGTCGACTATTCAATACCCTGCTTATGGTTAGGCTGTCGCCGTGTCCAGAGT GCGAAAGCAATGACACGCGGGACATCAGCGACACCAACTAATCACGCAACCAATACGATT
  781  ---------+---------+---------+---------+---------+---------+  840
       CGCTTTCGTTACTGTGCGCCCTGTAGTCGCTGTGGTTGATTAGTGCGTTGGTTATGCTAA GGGGTGTGGACTTTGACCGTTCCTGGCAATCAAAATGGCATGGTTTATGCTTACAAACTA
  841  ---------+---------+---------+---------+---------+---------+  900
       CCCCACACCTGAAACTGGCAAGGACCGTTAGTTTTACCGTACCAAATACGAATGTTTGAT ACTTTTGCTGACGGAACCGTTAGTGATTATGCTGGGTCAACTTATGGAACACTTTCTACA
  901  ---------+---------+---------+---------+---------+---------+  960
       TGAAAACGACTGCCTTGGCAATCACTAATACGACCCAGTTGAATACCTTGTGAAAGATGT AGTTCTGTCAGCAATACAACCAATGATCCTTATTCTATTGCGACGACACAAGGTGGAAAT
  961  ---------+---------+---------+---------+---------+---------+ 1020
       TCAAGACAGTCGTTATGTTGGTTACTAGGAATAAGATAACGCTGCTGTGTTCCACCTTTA CGTTCAGTTGTCGAATCGTCTGCAAACCTCGCGTCAAATCTGGCACTTGCGCAAGGCAAA
 1021  ---------+---------+---------+---------+---------+---------+ 1080
       GCAAGTCAACAGCTTAGCAGACGTTTGGAGCGCAGTTTAGACCGTGAACGCGTTCCGTTT TCTGCAACTTGGCGGGTAGCAAGTCCAACACAAGCCATCGTTGACGAACTACATATTCGT
 1081  ---------+---------+---------+---------+---------+---------+ 1140
       AGACGTTGAACCGCCCATCGTTCAGGTTGTGTTCGGTAGCAACTGCTTGATGTATAAGCA GATTTTACAAGCTCATCAACATCTGGTGTTTCGGCTGGTAATCGTGGTAAGTTTCTCGGA
 1141  ---------+---------+---------+---------+---------+---------+ 1200
       CTAAAATGTTCGAGTAGTTGTAGACCACAAAGCCGACCATTAGCACCATTCAAAGAGCCT GTGATTCAGTCAGGAACAACTGATCCAAATACAGGTACAGCGACTGGACTTGATTATCTG
 1201  ---------+---------+---------+---------+---------+---------+ 1260
       CACTAAGTCAGTCCTTGTTGACTAGGTTTATGTCCATGTCGCTGACCTGAACTAATAGAC AAAAACGAGGGTTTTAACTACATTCAACTTCATGCCAGCCAGTCAGTATGCGTCGGTCAA
 1261  ---------+---------+---------+---------+---------+---------+ 1320
       TTTTTGCTCCCAAAATTGATGTAAGTTGAAGTACGGTCGGTCAGTCATACGCAGCCAGTT CGAAGCGGGAACCGTACTACTGCGCAACCGAATAACTTCAACTGGGGATATGACCCACAA
 1321  ---------+---------+---------+---------+---------+---------+ 1380
       GCTTCGCCCTTGGCATGATGACGCGTTGGCTTATTGAAGTTGACCCCTATACTGGGTGTT ATGAATGGTACCAGAGCGAATATGCCAGTAATTCTGTCAATCCTGTCACACGTATTAAT
 1381  ---------+---------+---------+---------+---------+---------+ 1440
       TACTTTACCATGGTCTCGCTTATACGGTCATTAAGACAGTTAGGACAGTGTGCATAATTA GAAATGAAAGAAATGGTACAAGGCTTGCATACAAATGGGATTAGCGTGGTAATGGATATG
 1441  ---------+---------+---------+---------+---------+---------+ 1500
       CTTTACTTTCTTTACCATGTTCCGAACGTATGTTTACCCTAATCGCACCATTACCTATAC GTTCTCAATCACGTCTATAGTCAGTCAGCATCCGCTTTTGAAAAAGCCGAGCCGGGCTAT
 1501  ---------+---------+---------+---------+---------+---------+ 1560
       CAAGAGTTAGTGCAGATATCAGTCAGTCGTAGGCGAAAACTTTTTCGGCTCGGCCCGATA
```

```
                  -continued
     TATTTCCGCAAAAATACGCAATCTGGGTGTGGCAATGATACGGCGAGCAACCACGAAATG
1561 ---------+---------+---------+---------+---------+---------+ 1620
     ATAAAGGCGTTTTTATGCGTTAGACCCACACCGTTACTATGCCGCTCGTTGGTGCTTTAC TTTGGTAAATACATTATTGACTCTGTCACTTACTGGGCGAAAAATTATGATATTGACGGC
1621 ---------+---------+---------+---------+---------+---------+ 1680
     AAACCATTTATGTAATAACTGAGACAGTGAATGACCCGCTTTTTAATACTATAACTGCCG TTCCGTTTTGATGAAATGACACTTTTAGACAGCACGACTATGAATAAACTGCGTGCCGCA
1681 ---------+---------+---------+---------+---------+---------+ 1740
     AAGGCAAAACTACTTTACTGTGAAAATCTGTCGTGCTGATACTTATTTGACGCACGGCGT CTGACAGCACTTGACCCACATATTATCATGTATGGCGAAGGTTGGGGCGATTCTAATGCA
1741 ---------+---------+---------+---------+---------+---------+ 1800
     GACTGTCGTGAACTGGGTGTATAATAGTACATACCGCTTCCAACCCCGCTAAGATTACGT AATAATATTCCTGAAACGTCTATCAATAATTACAAAAATGTTCCTGGTATTGGTTTTTTC
1801 ---------+---------+---------+---------+---------+---------+ 1860
     TTATTATAAGGACTTTGCAGATAGTTATTAATGTTTTTACAAGGACCATAACCAAAAAAG AATCCTGGTGAACGTGACGCCATCAGTAATAATGGAGGTTCTGCAGGTGGATTCGCAGCA
1861 ---------+---------+---------+---------+---------+---------+ 1920
     TTAGGACCACTTGCACTGCGGTAGTCATTATTACCTCCAAGACGTCCACGTAAGCGTCGT GGAAATACGGCAAGTACTATAACGGTCGCAGGAGCACTTTTGGCTTCTGGAGGTTGGAAC
1921 ---------+---------+---------+---------+---------+---------+ 1980
     CCTTTATGCCGTTCATGATATTGCCAGCGTCCTCGTGAAAACCGAAGACCTCCAACCTTG GGAAATGGCACAGTGCAAGCTTTTTTGACGCCAAGCCAGTCTATCAATTATGTTGAATGT
1981 ---------+---------+---------+---------+---------+---------+ 2040
     CCTTTACCGTGTCACGTTCGAAAAAACTGCGGTTCGGTCAGATAGTTAATACAACTTACA GATGATAGCTTCACCTTAAATGACTCACTCTGGTCAGCTGATCCGAATGATTCTGTGGCG
2041 ---------+---------+---------+---------+---------+---------+ 2100
     GTACTATCGAAGTGGAATTTACTGAGTGAGACCAGTCGACTAGGCTTACTAAGACACCGC ACACATCAAGCGCGAGTGACGCTCGCAAATGCCACGAATATTCTTGCAAACGGTGTGACA
2101 ---------+---------+---------+---------+---------+---------+ 2160
     TGTGTAGTTCGCGCTCACTGCGAGCGTTTACGGTGCTTATAAGAACGTTTGCCACACTGT TTTATGGAAACAGGACAGGAGTTTGACCAGTCCAAATTAGTCAATCCGTCAAATCTGACG
2161 ---------+---------+---------+---------+---------+---------+ 2220
     AAATACCTTTGTCCTGTCCTCAAACTGGTCAGGTTTAATCAGTTAGGCAGTTTAGACTGC CCGCTCTCCCCTACACAGACACAGGCTTATCAATCGGGTAGTATGGAAAAACCTGCATGG
2221 ---------+---------+---------+---------+---------+---------+ 2280
     GGCGAGAGGGGATGTGTCTGTGTCCGAATAGTTAGCCCATCATACCTTTTTGGACGTACC TATCCTGCGTCATGGGATACTGCCAAAAATTCATACAATGGACTTTTTGGCTTGGCTAGT
2281 ---------+---------+---------+---------+---------+---------+ 2340
     ATAGGACGCAGTACCCTATGACGGTTTTTAAGTATGTTACCTGAAAAACCGAACCGATCA AATGGTACTTACTATGGCAATTATTGGCCAGGAAGTAATCTCTACACCCCAGTAGTTGCG
2341 ---------+---------+---------+---------+---------+---------+ 2400
     TTACCATGAATGATACCGTTAATAACCGGTCCTTCATTAGAGATGTGGGTCATCAACGC GGGGATGTAGTCAATGCCATGAATTGGGATAATGTCAAGGACAATCAAAATGCTGTTAAT
2401 ---------+---------+---------+---------+---------+---------+ 2460
     CCCCTACATCAGTTACGGTACTTAACCCTATTACAGTTCCTGTTAGTTTTACGACAATTA TTTATTGGAAATTTGATGAAATTTAAAAAATCCAATCCGCAATTTTGGCCTGATGATTAT
2461 ---------+---------+---------+---------+---------+---------+ 2520
     AAATAACCTTTAAACTACTTTAAATTTTTAGGTTAGGCGTTAAAACCGGACTACTAATA AGCAAACTTGCTTGGACTCCTACCAGTATAGGTGTAGAAAATGTCACAAATGCGTCAAAC
2521 ---------+---------+---------+---------+---------+---------+ 2580
     TCGTTTGAACGAACCTGAGCATGGTCATATCCACATCTTTTACAGTGTTTACGCAGTTTG GGAGTGATCACAGAAGAATTAACATCGGGTGCGACCAAATATTTAGTCATATTGAATGCT
2581 ---------+---------+---------+---------+---------+---------+ 2640
     CCTCACTAGTGTCTTCTTAATTGTAGCCCACGCTGGTTTATAAATCAGTATAACTTACGA AGCGGTAATTCGGTCAAAATTGGTCAAGGTGGTCAGTTTTATGGGCTGTCAAATTTGACA
2641 ---------+---------+---------+---------+---------+---------+ 2700
     TCGCCATTAAGCCAGTTTTAACCAGTTCCACCAGTCAAAATACCCCACAGTTTAAACTGT GGTAAAACTGTGATAATTTCTGACGATAGTAGCTTAACAGCTAATCAAGTTTTGAATAGC
2701 ---------+---------+---------+---------+---------+---------+ 2760
     CCATTTTGACACTATTAAAGACTGCTATCATCGAATTGTCGATTAGTTCAAAACTTATCG
```

```
                 -continued
     TCTGTCACTCTGTCAAATTTGACAGTCACCGTTATCCAACTTTCTAAATAA
2761 ---------+---------+---------+---------+---------+-      2811
     AGACAGTGAGACAGTTTAAACTGTCAGTGGCAATAGGTTGAAAGATTTATT
```

Ways of producing the novel plasmidic gene encoding the novel amylolytic enzyme which is secreted into the environment, according to the invention, are as follows: the plasmid DNA, previously isolated from the bacterial strain, favorably belonging to *Lactococcus* genus, encoding the amylolytic enzyme, is digested with restriction enzymes, favorably EcoRI, SacII, SalI, SmaI, SpeI, XhoI or XbaI. Subsequently, the excised fragment, favorably of size not smaller than 3.0 kb is ligated with a plasmid capable of replicating in bacterial cells, favorably those of *Lactococcus* genus, especially pIL253, pGKV210 or pIL252 also digested previously with restriction enzymes, favorably with EcoRI, SalI, or SmaI, after which the two DNA fragments are recombined together and introduced by means of electroporation into bacterial cells, which are grown in a known manner, and from the cultivated population, cells possessing the novel gene encoding the novel amylolytic enzyme are isolated in a known way.

In the method according to the invention bacterial strains into which the recombined DNA is introduced are favorably used *Lactococcus lactis* MG1363, *Lactococcus lactis* IL1403 or *Lactococcus lactis* IBB140.

In the method according to the invention colonies producing the amylolytic enzyme and carrying the novel gene are positively separated by inoculation into fresh liquid medium with antibiotic and starch if necessary.

The novel enzyme secreted into the environment, encoded by the novel plasmidic gene according to the invention, has the following amino acid structure (SEQ. ID NO. 5):

enzyme's activity is in a range from 35°-45° C. as shown on graph (FIG. 2), and is thermally inactivated at temperatures higher than 50° C. as shown on graph (FIG. 3).

Application of the amylolytic enzyme encoded by the novel gene according to the invention, in fermentation of plant material, favorably starch, pullulan, amylose, amylopectin, feed production, obtaining glucose, lactic acid and production of probiotic specimens, probiotic-containing food, feed and fodder, according to the invention is based on the fact that its gene is introduced into the structure of the bacterial strain, favorably the strains of *Lactococcus lactis* IBB500, IBB501, IBB502, IBB140 and subsequently of applying the strains obtained in fermentations of plant material or milk or in biomass production.

The gene according to the invention has been sequenced and the sequence obtained indicates that it belongs to the family of pullulanase encoding genes. The analysis of the gene's promoter region as well as functional studies suggest that the expression of this gene undergoes catabolic repression.

General Characteristics of the Amylolytic Enzyme

From the comparison of features of pullulanases from studied *L. lactis* IBB500 and IBB502 strains it can be concluded that we are dealing with an enzyme produced in two organisms. Pullulanase deriving from both of the strains had the optimum pH of 4.4 and reached the optimal temperature at 45° C. (FIGS. 1, 2).

```
  1  MKKTKLRICL  FPIVLLISFT  LLSNGTGKQI  VFATSSSEYA  TQALSDEKNA

51  TQNNDFTSFD  IKWAYEGTDL  GFNYSTTSTT  FKIWSPTATS  VQLISYGTNT

101  NPTAAQVSAK  AMTRGTSATP  TNHATNTIGV  WTLTVPGNQN  GMVYAYKLTF

151  ADGTVSDYAG  STYGTLSTSS  VSNTTNDPYS  IATTQGGNRS  VVESSANLAS

201  NLALAQGKSA  TWRVASPTQA  IVDELHIRDF  TSSSTSGVSA  GNRGKFLGVI

251  QSGTTDPNTG  TATGLDYLKN  EGFNYIQLHA  SQSVCVGQRS  GNRTTAQPNN

301  FNWGYDPQMK  WYQSEYASNS  VNPVTRINEM  KEMVQGLHTN  GISVVMDMVL

351  NHVYSQSASA  FEKAEPGYYF  RKNTQSGCGN  DTASNHEMFG  KYIIDSVTYW

401  AKNYDIDGFR  FDEMTLLDST  TMNKLRAALT  ALDPHIIMYG  EGWGDSNANN

451  IPETSINNYK  NVPGIGFFNP  GERDAISNNG  GSAGGFAAGN  TASTITVAGA

501  LLASGGWNGN  GTVQAFLTPS  QSINYVECHD  SFTLNDSLWS  ADPNDSVATH

551  QARVTLANAT  NILANGVTFM  ETGQEFDQSK  LVNPSNLTPL  SPTQTQAYQS

601  GSMEKPAWYP  ASWDTAKNSY  NGLFGLASNG  TYYGNYWPGS  NLYTPVVAGD

651  VVNAMNWDNV  KDNQNAVNFI  GNLMKFKKSN  PQFWPDDYSK  LAWTPTSIGV

701  ENVTNASNGV  ITEELTSGAT  KYLVILNASG  NSVKIGQGGQ  FYGVSNLTGK

751  TVIISDDSSL  TANQVLNSSV  TLSNLTVTVI  QLSK
```

This enzyme exhibits a unique set of profitable features, especially showing activity in a wide range of acid pH from 3.5 to 5.5 as shown on graph (FIG. 1) while its optimum is at a pH 4.4. At the same time the optimal temperature of the One should note the rather narrow pH range of the enzyme's activity between pH 3.5-5.5 as well as the fact that it is significantly lower than for pullulanases deriving from other bacteria (Ara K., Igarashi K., Saeki K., Kawai S., and S., Ito. 1992. Biosci. Biotech. Biochem. 56:62; Kim Ch., Nashiru O., J., Ko. 1996. FEMS Microbiology Letters 138: 147; Takasaki Y. 1987. Agric. Biol. Chem., 51:9).

The enzyme obtained with the help of the novel gene according to the invention, shows homology to amylolytic enzymes of the pullulanase group and the highest homology was found to pullulanase from *Termotoga maritima*. In the amino acid sequence of pullulanase from *L. lactis* IBB500 four conserved motives, characteristic for many amylolytic enzymes were identified. The nucleotide sequence of pul gene was preceded by a RBS typical for *Lactococcus* in front of which a long 500-nucleotide non-coding region was identified.

The thorough analysis of the non-coding region upstream of the pul gene showed the presence of several putative promoter sequences. Due to the earlier observations of the effect of glucose on pullulanase production, from which was concluded that the expression of the pul gene may be regulated by catabolic repression, the promoter region was analyzed for the presence of the cre motive, characteristic for this mechanism of regulation (Weickert M. J. and S. Adhya. 1992. J. Biol. Chem. 267: 15869). It was determined that the sequence homologous to the 14-nucleotide cre sequence is present in the analyzed promoter region. This observation strongly supported the earlier hypothesis. Another argument for the validity of this hypothesis was acquired during experiments on the influence of glucose as well as starch and its derivates on the pullulanase production in the IBB500 strain. In the process it was determined that starch and its derivatives induce pullulanase production although at different levels, while in the presence of glucose the repression of production of this enzyme is observed (Domań M., E. Czerniec, Z. Targoński and J. Bardowski. 2000. Food Biotechnology 17:67, Elsevier Science B.V., Amsterdam).

HERE BELOW THE EXAMPLES OF REALIZATION ARE PRESENTED

Materials and Methods

Bacterial Strains, Growth Conditions and Plasmids Used.

Bacterial strains and plasmids used in these studies are shown in Table 1. *Lactococcus lactis* strains were grown in BHI medium (Oxoid, England) or M17 (Difco, USA), at the temperature of 28° C., *Escherichia coli* in Luria-Bertani medium (LB), at the temperature of 37° C. Where necessary for selection, the following antibiotics were used: erythromycin—5 µg/ml for *L. lactis* and ampicyline—100 µg/ml for *E. coli*.

Example I

Plasmid DNA was isolated from *Lactococcus lactis* IBB500 bacterial strain encoding the amylolytic enzyme. Subsequently, it was digested with EcoRI restriction enzyme, then the excised fragment not smaller that 8.0 kb was ligated with a plasmid capable of replicating in *Lactococcus* bacterial cells—pIL253, digested previously also with EcoRI restriction enzyme. Both DNAs were recombined with each other and introduced by the method of electroporation into *Lactococcus lactis* cells which were grown and from the cultivated population cells carrying the novel gene of the structure according to the invention were isolated by inoculation into fresh liquid medium with antibiotic and starch.

*L. lactis* cells were transformed by method of electroporation (Holo H. and I. F. Nes. 1989. Appl. Environ. Microbiol. 55: 3119).

The remaining molecular biology techniques used in the example were carried out according to the standard methodology (Sambrook J., E. F. Fritsch and T. Maniatis. 1989. Molecular cloning: a laboratory manual, $2^{nd}$ edition. Cold Spring Harbor Laboratory, Cold Spring Harbor, N.Y.).

Example II

Plasmid DNA was isolated from *Lactococcus lactis* IBB500 bacterial strain encoding the amylolytic enzyme. Subsequently, it was digested with XhoI restriction enzyme, the excised fragment of size not smaller than 5.0 kb was ligated with a plasmid capable of replicating in *Lactococcus* bacterial cells—pIL253, digested previously also with XhoI. Both DNAs were then recombined with each other and introduced by method of electroporation into *Lactococcus lactis* cells which were grown and from the cultivated population cells carrying the novel gene of the structure according to the invention was selected by inoculation into fresh liquid medium with antibiotic and starch.

*L. lactis* cells were transformed by method of electroporation (Holo H. and I. F. Nes. 1989. Appl. Environ. Microbiol. 55: 3119).

The remaining molecular biology techniques used in the example were carried out according to the standard methodology (Sambrook J., E. F. Fritsch and T. Maniatis. 1989. Molecular cloning: a laboratory manual, $2^{nd}$ edition. Cold Spring Harbor Laboratory, Cold Spring Harbor, N.Y.).

Example III

The structure of the nucleotide sequence of the novel gene and the amino acid sequence of the amylolytic enzyme encoded by this gene according to the invention was determined by sequencing a PstI 1.5 kb fragment of the pIBB502 plasmid, carrying a part of the novel gene, which was previously cloned in pBluescript plasmid (Stratagene), what generated the pIBB504 plasmid. This plasmid was used to sequence the cloned fragment from both sides. Transformation of *E. coli* cells was carried out according to the standard method with the use of $CaCl_2$ (Sambrook J., E. F. Fritsch and T. Maniatis. 1989. Molecular cloning: a laboratory manual, $2^{nd}$ edition. Cold Spring Harbor Laboratory, Cold Spring Harbor, N.Y.).

The complete nucleotide sequence of the fragment and of the lacking part of the novel gene encoding the amylolytic enzyme were obtained by using the sequencing method named "primer walking". For DNA sequencing BigDye Terminator set (Promega, USA), PCR machine model 2400 (Perkin-Elmer) and sequencer ABI377 (Applied Biosystem, USA) were used. The nucleotide and amino acid sequences obtained were analyzed using the GCG programs (Genetics Computer Group. 1991. Program manual for the GCG package, version 7, April 1991. Genetic Computer Group, Madison, Wis., USA) and BLAST (Altschul S. F., W. Gish, W. Miller, E. W. Myers and D. J. Lipman. (1990), J. Mol. Biol. 215: 403).

Example IV

For determining the amylolytic activity two tests—quantitative and qualitative were applied.

Qualitative Test on Plates

Bacterial strains were plated on BHI with 0.5% starch and incubated in 28° C. for two days. Subsequently, the grown colonies were overlayed with Lugol reagent, which colors the non-degraded starch dark blue. A clear zone of non-colored medium surrounded colonies that secrete the amylolytic enzyme into the environment.

Quantitative Determination of Enzyme Activity

In this test a modified method was used to determine the activity of extracellular amylase (Nicholson W. and P. Setlow. 1990. Sporulation, germination and outgrowth, p 433. W C. R. Harwood and S. M. Cutting (ed.), Molecular Biology for Bacillus. John Wiley and Sons Ltd., Chichester, United Kingdom).

In this method the enzymatic activity was determined in the supernatant of the culture: to 200 µl of this supernatant 800 µl of the substrate (0.025% starch in 10 mM Tris-HCl-3 mM potassium acetate-25 mM $CaCl_2$, pH 4.4) was added and incubated for 30 min. at 37° C. The reaction was stopped by adding 400 µl of Lugol reagent and the absorption was measured at wavelength of 620 nm [$A_{620}$]. As a control non-inoculated medium was used.

One unit of amylolytic activity (1 U) was established as the amount of enzyme, which in the conditions of the test, generated the decrease of the substrate's absorption $A_{620}$ by 0.1 compared to the control.

TABLE 1

Strains and plasmids.

| Strains and plasmids | Genotype | Source |
|---|---|---|
| | *Lactococcus lactis* | |
| IBB 500 | amy+ wild type strain isolated from plant material | IBB PAN collection |
| IBB 501 | amy+ MG 1363 with pIBB501 | this work |
| IBB 502 | amy+ derivative of MG 1363 with pIBB502 | this work |
| IBB 140 | amy+ IBB140 with pIBB502 | this work |
| IL 1403 | amy−, plamid-free | A. Chopin, France |
| MG 1363 | amy−, plamid-free | M. Gasson, England |
| | *Eschercia coli* | |
| TG1 | supE thi Δ(lac-proAB) hsd (F'+ traD proAB lacl<sup>q</sup> Z M15) | (Gibson, 1984) |
| IBB 504 | amy− derivative of TG1 with pIBB504 | this work |
| | Plasmids | |
| pIBB500 | 30-kb, wild type plasmid with amy+ gene | this work |
| pIBB501 | 20-kb fragment of pIBB500 with amy+ gene cloned in pIL253 | this work |
| pIBB502 | 13-kb derivative of pIBB501 with amy+ gene | this work |
| pIBB504 | 1.5-kb PstI fragment from pIBB502 in pSKII+ | this work |
| pBluescript SKII+ | Amp<sup>R</sup>, vector for cloning and DNA sequencing | Stratagene, USA |
| pIL253 | Ery<sup>R</sup>, vector for gene cloning | A. Chopin, France |

The invention claimed is:

1. An isolated polypeptide comprising the amino acid sequence of SEQ ID No. 5.

2. The polypeptide according to claim 1 which is encoded by the nucleotide sequence of SEQ ID No. 1.

\* \* \* \* \*

SEQUENCE LISTING

```
<160> NUMBER OF SEQ ID NOS: 5

<210> SEQ ID NO 1
<211> LENGTH: 2355
<212> TYPE: DNA
<213> ORGANISM: Lactococcus lactis

<400> SEQUENCE: 1
atgaaaaaaa caaaattaag aatttgtctt ttcccaatcg tactgcttat cagttttaca      60
ttgctatcca atggaactgg taaacagatt gtttttgcta catcttcatc agaatatgct     120
acacaagctc tgtctgacga gaaaaatgcc acacaaaaca atgattttac atctttttgat    180 ataaaatggg cctatgaagg gacagatttg ggatttaact attcaacaac cagtactact    240
ttcaaaatct ggtcaccaac tgcgacgagc gtgcagctga taagttatgg gacgaatacc     300
aatccgacag cggcacaggt ctcagcgaaa gcaatgacac gcgggacatc agcgacacca     360
actaatcacg caaccaatac gattggggtg tggactttga ccgttcctgg caatcaaaat     420
ggcatggttt atgcttacaa actaactttt gctgacggaa ccgttagtga ttatgctggg     480
tcaacttatg gaacactttc tacaagttct gtcagcaata caaccaatga tccttattct     540
attgcgacga cacaaggtgg aaatcgttca gttgtcgaat cgtctgcaaa cctcgcgtca     600
aatctggcac ttgcgcaagg caaatctgca acttggcggg tagcaagtcc aacacaagcc     660
atcgttgacg aactacatat tcgtgatttt acaagctcat caacatctgg tgtttcggct     720
ggtaatcgtg gtaagtttct cggagtgatt cagtcaggaa caactgatcc aaatacaggt     780
```

```
acagcgactg gacttgatta tctgaaaaac gagggtttta actacattca acttcatgcc    840
agccagtcag tatgcgtcgg tcaacgaagc gggaaccgta ctactgcgca accgaataac    900
ttcaactggg gatatgaccc acaaatgaaa tggtaccaga gcgaatatgc cagtaattct    960
gtcaatcctg tcacacgtat taatgaaatg aaagaaatgg tacaaggctt gcatacaaat   1020
gggattagcg tggtaatgga tatggttctc aatcacgtct atagtcagtc agcatccgct   1080
tttgaaaaag ccgagccggg ctattatttc cgcaaaaata cgcaatctgg gtgtggcaat   1140
gatacggcga gcaaccacga aatgtttggt aaatacatta ttgactctgt cacttactgg   1200
gcgaaaaatt atgatattga cggcttccgt tttgatgaaa tgacactttt agacagcacg   1260
actatgaata aactgcgtgc cgcactgaca gcacttgacc cacatattat catgtatggc   1320
gaaggttggg gcgattctaa tgcaaataat attcctgaaa cgtctatcaa taattacaaa   1380
aatgttcctg gtattggttt tttcaatcct ggtgaacgtg acgccatcag taataatgga   1440
ggttctgcag gtggattcgc agcaggaaat acggcaagta ctataacggt cgcaggagca   1500
cttttggctt ctggaggttg gaacggaaat ggcacagtgc aagcttttt gacgccaagc    1560 cagtctatca attatgttga atgtcatgat agcttcacct taaatgactc actctggtca   1620
gctgatccga atgattctgt ggcgacacat caagcgcgag tgacgctcgc aaatgccacg   1680
aatattcttg caaacggtgt gacatttatg gaaacaggac aggagtttga ccagtccaaa   1740
ttagtcaatc cgtcaaatct gacgccgctc tcccctacac agacacaggc ttatcaatcg   1800
ggtagtatgg aaaaacctgc atggtatcct gcgtcatggg atactgccaa aaattcatac   1860
aatggacttt ttggcttggc tagtaatggt acttactatg gcaattattg gccaggaagt   1920
aatctctaca ccccagtagt tgcggggat gtagtcaatg ccatgaattg ggataatgtc   1980
aaggacaatc aaaatgctgt taattttatt ggaaatttga tgaaatttaa aaaatccaat   2040
ccgcaatttt ggcctgatga ttatagcaaa cttgcttgga ctcctaccag tataggtgta   2100
gaaaatgtca caaatgcgtc aaacggagtg atcacagaag aattaacatc gggtgcgacc   2160
aaatatttag tcatattgaa tgctagcggt aattcggtca aaattggtca aggtggtcag   2220
ttttatgggg tgtcaaattt gacaggtaaa actgtgataa tttctgacga tagtagctta   2280
acagctaatc aagttttgaa tagctctgtc actctgtcaa atttgacagt caccgttatc   2340
caactttcta aataa                                                    2355

<210> SEQ ID NO 2
<211> LENGTH: 2355
<212> TYPE: DNA
<213> ORGANISM: Lactococcus lactis

<400> SEQUENCE: 2 tactttttt gttttaattc ttaaacagaa aagggttagc atgacgaata gtcaaaatgt     60
aacgataggt taccttgacc atttgtctaa caaaaacgat gtagaagtag tcttatacga    120
tgtgttcgag acagactgct cttttacgg tgtgttttgt tactaaaatg tagaaaacta    180
tattttaccc ggatacttcc ctgtctaaac cctaaattga taagttgttg gtcatgatga    240
aagttttaga ccagtggttg acgctgctcg cacgtcgact attcaatacc ctgcttatgg    300
ttaggctgtc gccgtgtcca gagtcgcttt cgttactgtg cgccctgtag tcgctgtggt    360
tgattagtgc gttggttatg ctaaccccac acctgaaact ggcaaggacc gttagtttta    420
ccgtaccaaa tacgaatgtt tgattgaaaa cgactgcctt ggcaatcact aatacgaccc    480
```

-continued

```
agttgaatac cttgtgaaag atgttcaaga cagtcgttat gttggttact aggaataaga      540
taacgctgct gtgttccacc tttagcaagt caacagctta gcagacgttt ggagcgcagt      600
ttagaccgtg aacgcgttcc gtttagacgt tgaaccgccc atcgttcagg ttgtgttcgg      660
tagcaactgc ttgatgtata agcactaaaa tgttcgagta gttgtagacc acaaagccga      720
ccattagcac cattcaaaga gcctcactaa gtcagtcctt gttgactagg tttatgtcca      780
tgtcgctgac ctgaactaat agacttttg ctcccaaaat tgatgtaagt tgaagtacgg      840
tcggtcagtc atacgcagcc agttgcttcg cccttggcat gatgacgcgt tggcttattg      900
aagttgaccc ctatactggg tgtttacttt accatggtct cgcttatacg gtcattaaga      960
cagttaggac agtgtgcata attactttac tttctttacc atgttccgaa cgtatgttta     1020
ccctaatcgc accattacct ataccaagag ttagtgcaga tatcagtcag tcgtaggcga     1080 aaacttttc ggctcggccc gataataaag gcgttttat gcgttagacc cacaccgtta     1140
ctatgccgct cgttggtgct ttacaaacca tttatgtaat aactgagaca gtgaatgacc     1200 cgcttttaa tactataact gccgaaggca aaactacttt actgtgaaaa tctgtcgtgc     1260
tgatacttat ttgacgcacg gcgtgactgt cgtgaactgg gtgtataata gtacataccg     1320
cttccaaccc cgctaagatt acgtttatta taaggacttt gcagatagtt attaatgttt     1380
ttacaaggac cataaccaaa aaagttagga ccacttgcac tgcggtagtc attattacct     1440
ccaagacgtc cacctaagcg tcgtccttta tgccgttcat gatattgcca gcgtcctcgt     1500
gaaaaccgaa gacctccaac cttgccttta ccgtgtcacg ttcgaaaaaa ctgcggttcg     1560
gtcagatagt taatacaact tacagtacta tcgaagtgga atttactgag tgagaccagt     1620
cgactaggct tactaagaca ccgctgtgta gttcgcgctc actgcgagcg tttacggtgc     1680
ttataagaac gtttgccaca ctgtaaatac ctttgtcctg tcctcaaact ggtcaggttt     1740
aatcagttag gcagtttaga ctgcggcgag agggatgtg tctgtgtccg aatagttagc     1800
ccatcatacc ttttggacg taccatagga cgcagtaccc tatgacggtt tttaagtatg     1860
ttacctgaaa aaccgaaccg atcattacca tgaatgatac cgttaataac cggtccttca     1920
ttagagatgt ggggtcatca acgcccccta catcagttac ggtacttaac cctattacag     1980
ttcctgttag ttttacgaca attaaaataa cctttaaact actttaaatt ttttaggtta     2040
ggcgttaaaa ccggactact aatatcgttt gaacgaacct gaggatggtc atatccacat     2100
cttttacagt gtttacgcag tttgcctcac tagtgtcttc ttaattgtag cccacgctgg     2160
tttataaatc agtataactt acgatcgcca ttaagccagt tttaaccagt tccaccagtc     2220 aaaataccc acagtttaaa ctgtccattt tgacactatt aaagactgct atcatcgaat     2280
tgtcgattag ttcaaaactt atcgagacag tgagacagtt taaactgtca gtggcaatag     2340
gttgaaagat ttatt                                                     2355
```

<210> SEQ ID NO 3
<211> LENGTH: 2811
<212> TYPE: DNA
<213> ORGANISM: Lactococcus lactis

<400> SEQUENCE: 3

```
ttacgttagc tggagaatcc accgtgtgga gcctccgtct cacggttgct ccgtgttacg       60
gtaattccgc tgctataaag taataactaa taacaaatta aatagcagta taaaattttg      120
ataatttgaa gattatttta atatttacct gaataacact ttagaaaact gaaatatcta      180
taactccaga tcaatagtgg aaatacgtac aatttgatat aagagatttt tgtatcaaaa      240
```

-continued

```
aaaattttttt taaacaaaat gcactaaaag atttttttgt gttgctgaga ggttgcaaaa      300
tgataccgca aggtatataa tggttacgta attagtgcaa gcgcttgcat tttttgtgaa      360
aaaagtcctt ttatttattt atcttattgc tttgaaagat attgttaaaa ataaataaaa      420
tcgttataaa ctcaatataa taaggagagc taaataatga aaaaaacaaa attaagaatt      480
tgtcttttcc caatcgtact gcttatcagt tttacattgc tatccaatgg aactggtaaa      540
cagattgttt ttgctacatc ttcatcagaa tatgctacac aagctctgtc tgacgagaaa      600
aatgccacac aaaacaatga ttttacatct tttgatataa aatgggccta tgaagggaca      660
gatttgggat ttaactattc aacaaccagt actactttca aaatctggtc accaactgcg      720
acgagcgtgc agctgataag ttatgggacg aataccaatc cgacagcggc acaggtctca      780
gcgaaagcaa tgacacgcgg gacatcagcg acaccaacta atcacgcaac caatacgatt      840
ggggtgtgga ctttgaccgt tcctggcaat caaaatggca tggtttatgc ttacaaacta      900
acttttgctg acggaaccgt tagtgattat gctgggtcaa cttatggaac actttctaca      960
agttctgtca gcaatacaac caatgatcct tattctattg cgacgacaca aggtggaaat     1020
cgttcagttg tcgaatcgtc tgcaaacctc gcgtcaaatc tggcacttgc gcaaggcaaa     1080
tctgcaactt ggcgggtagc aagtccaaca caagccatcg ttgacgaact acatattcgt     1140
gattttacaa gctcatcaac atctggtgtt tcggctggta atcgtggtaa gtttctcgga     1200
gtgattcagt caggaacaac tgatccaaat acaggtacag cgactggact tgattatctg     1260
aaaaacgagg gttttaacta cattcaactt catgccagcc agtcagtatg cgtcggtcaa     1320
cgaagcggga accgtactac tgcgcaaccg aataacttca actggggata tgacccacaa     1380
atgaaatggt accagagcga atatgccagt aattctgtca atcctgtcac acgtattaat     1440
gaaatgaaag aaatggtaca aggcttgcat acaaatggga ttagcgtggt aatggatatg     1500
gttctcaatc acgtctatag tcagtcagca tccgcttttg aaaaagccga gccgggctat     1560
tatttccgca aaaatacgca atctgggtgt ggcaatgata cggcgagcaa ccacgaaatg     1620
tttggtaaat acattattga ctctgtcact tactgggcga aaaattatga tattgacggc     1680
ttccgttttg atgaaatgac acttttagac agcacgacta tgaataaact gcgtgccgca     1740
ctgacagcac ttgacccaca tattatcatg tatggcgaag gttggggcga ttctaatgca     1800
aataatattc ctgaaacgtc tatcaataat tacaaaaatg ttcctggtat tggttttttc     1860
aatcctggtg aacgtgacgc catcagtaat aatggaggtt ctgcaggtgg attcgcagca     1920
ggaaatacgg caagtactat aacggtcgca ggagcacttt tggcttctgg aggttggaac     1980
ggaaatggca cagtgcaagc ttttttgacg ccaagccagt ctatcaatta tgttgaatgt     2040
catgatagct tcaccttaaa tgactcactc tggtcagctg atccgaatga ttctgtggcg     2100
acacatcaag cgcgagtgac gctcgcaaat gccacgaata ttcttgcaaa cggtgtgaca     2160
tttatggaaa caggacagga gttgaccagt ccaaattagt caatccgtc aaatctgacg     2220
ccgctctccc ctacacagac acaggcttat caatcgggta gtatgaaaaa acctgcatgg     2280
tatcctgcgt catgggatac tgccaaaaat tcatacaatg gactttttgg cttggctagt     2340
aatggtactt actatggcaa ttattggcca ggaagtaatc tctacacccc agtagttgcg     2400
ggggatgtag tcaatgccat gaattgggat aatgtcaagg acaatcaaaa tgctgttaat     2460
tttattggaa atttgatgaa atttaaaaaa tccaatccgc aatttttgcc tgatgattat     2520
agcaaacttg cttggactcc taccagtata ggtgtagaaa atgtcacaaa tgcgtcaaac     2580
```

-continued

```
ggagtgatca cagaagaatt aacatcgggt gcgaccaaat atttagtcat attgaatgct    2640
agcggtaatt cggtcaaaat tggtcaaggt ggtcagtttt atggggtgtc aaatttgaca    2700
ggtaaaactg tgataatttc tgacgatagt agcttaacag ctaatcaagt tttgaatagc    2760
tctgtcactc tgtcaaattt gacagtcacc gttatccaac tttctaaata a             2811

<210> SEQ ID NO 4
<211> LENGTH: 2811
<212> TYPE: DNA
<213> ORGANISM: Lactococcus lactis

<400> SEQUENCE: 4
aatgcaatcg acctcttagg tggcacacct cggaggcaga gtgccaacga ggcacaatgc      60
cattaaggcg acgatatttc attattgatt attgtttaat ttatcgtcat attttaaaac     120
tattaaactt ctaataaaat tataaatgga cttattgtga aatcttttga ctttatagat     180
attgaggtct agttatcacc tttatgcatg ttaaactata ttctctaaaa acatagtttt     240
ttttaaaaaa atttgtttta cgtgattttc taaaaaaaca caacgactct ccaacgtttt     300
actatggcgt tccatatatt accaatgcat taatcacgtt cgcgaacgta aaaaacactt     360
ttttcaggaa ataaataaa tagaataacg aaactttcta taacaatttt tatttatttt     420
agcaatattt gagttatatt attcctctcg atttattact ttttttgttt taattcttaa     480
acagaaaagg gttagcatga cgaatagtca aaatgtaacg ataggttacc ttgaccattt     540
gtctaacaaa aacgatgtag aagtagtctt atacgatgtg ttcgagacag actgctcttt     600
ttacggtgtg ttttgttact aaaatgtaga aaactatatt ttacccggat acttccctgt     660
ctaaacccta aattgataag ttgttggtca tgatgaaagt tttagaccag tggttgacgc     720
tgctcgcacg tcgactattc aatacctgc ttatggttag gctgtcgccg tgtccagagt     780
cgctttcgtt actgtgcgcc ctgtagtcgc tgtggttgat tagtgcgttg gttatgctaa     840
ccccacacct gaaactggca aggaccgtta gttttaccgt accaaatacg aatgtttgat     900
tgaaaacgac tgccttggca atcactaata cgacccagtt gaatacccttg tgaaagatgt     960 tcaagacagt cgttatgttg gttactagga ataagataac gctgctgtgt tccacccttta   1020 gcaagtcaac agcttagcag acgtttggag cgcagtttag accgtgaacg cgttccgttt    1080
agacgttgaa ccgcccatcg ttcaggttgt gttcggtagc aactgcttga tgtataagca    1140
ctaaaatgtt cgagtagttg tagaccacaa agccgaccat tagcaccatt caaagagcct    1200
cactaagtca gtccttgttg actaggttta tgtccatgtc gctgacctga actaatagac    1260 ttttgctcc caaaattgat gtaagttgaa gtacggtcgg tcagtcatac gcagccagtt    1320
gcttcgccct tggcatgatg acgcgttggc ttattgaagt tgaccccat actgggtgtt    1380 tactttacca tggtctcgct tatacggtca ttaagacagt taggacagtg tgcataatta    1440
ctttactttc tttaccatgt tccgaacgta tgtttaccct aatcgcacca ttacctatac    1500
caagagttag tgcagatatc agtcagtcgt aggcgaaaac ttttcggct cggcccgata    1560 ataaaggcgt ttatatgcgt tagacccaca ccgttactat gccgctcgtt ggtgctttac    1620
aaaccattta tgtaataact gagacagtga atgacccgct ttttaatact ataactgccg    1680
aaggcaaaac tactttactg tgaaaatctg tcgtgctgat acttatttga cgcacggcgt    1740
gactgtcgtg aactgggtgt ataatagtac ataccgcttc caaccccgct aagattacgt    1800
ttattataag gactttgcag atagttatta atgttttttac aaggaccata accaaaaaag    1860
ttaggaccac ttgcactgcg gtagtcatta ttacctccaa gacgtccacc taagcgtcgt    1920
```

-continued

```
cctttatgcc gttcatgata ttgccagcgt cctcgtgaaa accgaagacc tccaaccttg    1980
cctttaccgt gtcacgttcg aaaaaactgc ggttcggtca gatagttaat acaacttaca    2040
gtactatcga agtggaattt actgagtgag accagtcgac taggcttact aagacaccgc    2100
tgtgtagttc gcgctcactg cgagcgttta cggtgcttat aagaacgttt gccacactgt    2160 aaatacctt gtcctgtcct caaactggtc aggtttaatc agttaggcag tttagactgc     2220
ggcgagaggg gatgtgtctg tgtccgaata gttagcccat catacctttt tggacgtacc    2280
ataggacgca gtaccctatg acggttttta agtatgttac ctgaaaaacc gaaccgatca    2340
ttaccatgaa tgataccgtt aataaccggt ccttcattag agatgtgggg tcatcaacgc    2400
cccctacatc agttacggta cttaacccta ttacagttcc tgttagtttt acgacaatta    2460
aaataacctt taaactactt taaattttt aggttaggcg ttaaaaccgg actactaata    2520
tcgtttgaac gaacctgagg atggtcatat ccacatcttt tacagtgttt acgcagtttg    2580
cctcactagt gtcttcttaa ttgtagccca cgctggttta taaatcagta taacttacga    2640
tcgccattaa gccagtttta accagttcca ccagtcaaaa taccccacag tttaaactgt    2700
ccattttgac actattaaag actgctatca tcgaattgtc gattagttca aaacttatcg    2760
agacagtgag acagtttaaa ctgtcagtgg caataggttg aaagatttat t             2811
```

<210> SEQ ID NO 5
<211> LENGTH: 784
<212> TYPE: PRT
<213> ORGANISM: Lactococcus lactis

<400> SEQUENCE: 5

```
Met Lys Lys Thr Lys Leu Arg Ile Cys Leu Phe Pro Ile Val Leu Leu
 1               5                   10                  15

Ile Ser Phe Thr Leu Leu Ser Asn Gly Thr Gly Lys Gln Ile Val Phe
                20                  25                  30

Ala Thr Ser Ser Ser Glu Tyr Ala Thr Gln Ala Leu Ser Asp Glu Lys
            35                  40                  45

Asn Ala Thr Gln Asn Asn Asp Phe Thr Ser Phe Asp Ile Lys Trp Ala
        50                  55                  60

Tyr Glu Gly Thr Asp Leu Gly Phe Asn Tyr Ser Thr Thr Ser Thr Thr
 65                  70                  75                  80

Phe Lys Ile Trp Ser Pro Thr Ala Thr Ser Val Gln Leu Ile Ser Tyr
                 85                  90                  95

Gly Thr Asn Thr Asn Pro Thr Ala Ala Gln Val Ser Ala Lys Ala Met
            100                 105                 110

Thr Arg Gly Thr Ser Ala Thr Pro Thr Asn His Ala Thr Asn Thr Ile
        115                 120                 125

Gly Val Trp Thr Leu Thr Val Pro Gly Asn Gln Asn Gly Met Val Tyr
    130                 135                 140

Ala Tyr Lys Leu Thr Phe Ala Asp Gly Thr Val Ser Asp Tyr Ala Gly
145                 150                 155                 160

Ser Thr Tyr Gly Thr Leu Ser Thr Ser Ser Val Ser Asn Thr Thr Asn
                165                 170                 175

Asp Pro Tyr Ser Ile Ala Thr Thr Gln Gly Gly Asn Arg Ser Val Val
            180                 185                 190

Glu Ser Ser Ala Asn Leu Ala Ser Asn Leu Ala Leu Ala Gln Gly Lys
        195                 200                 205

Ser Ala Thr Trp Arg Val Ala Ser Pro Thr Gln Ala Ile Val Asp Glu
```

-continued

```
            210                 215                 220
Leu His Ile Arg Asp Phe Thr Ser Ser Thr Ser Gly Val Ser Ala
225                 230                 235                 240

Gly Asn Arg Gly Lys Phe Leu Gly Val Ile Gln Ser Gly Thr Thr Asp
                245                 250                 255

Pro Asn Thr Gly Thr Ala Thr Gly Leu Asp Tyr Leu Lys Asn Glu Gly
                260                 265                 270

Phe Asn Tyr Ile Gln Leu His Ala Ser Gln Ser Val Cys Val Gly Gln
                275                 280                 285

Arg Ser Gly Asn Arg Thr Thr Ala Gln Pro Asn Asn Phe Asn Trp Gly
290                 295                 300

Tyr Asp Pro Gln Met Lys Trp Tyr Gln Ser Glu Tyr Ala Ser Asn Ser
305                 310                 315                 320

Val Asn Pro Val Thr Arg Ile Asn Glu Met Lys Glu Met Val Gln Gly
                325                 330                 335

Leu His Thr Asn Gly Ile Ser Val Val Met Asp Met Val Leu Asn His
                340                 345                 350

Val Tyr Ser Gln Ser Ala Ser Ala Phe Glu Lys Ala Glu Pro Gly Tyr
                355                 360                 365

Tyr Phe Arg Lys Asn Thr Gln Ser Gly Cys Gly Asn Asp Thr Ala Ser
370                 375                 380

Asn His Glu Met Phe Gly Lys Tyr Ile Ile Asp Ser Val Thr Tyr Trp
385                 390                 395                 400

Ala Lys Asn Tyr Asp Ile Asp Gly Phe Arg Phe Asp Glu Met Thr Leu
                405                 410                 415

Leu Asp Ser Thr Thr Met Asn Lys Leu Arg Ala Ala Leu Thr Ala Leu
                420                 425                 430

Asp Pro His Ile Ile Met Tyr Gly Glu Gly Trp Gly Asp Ser Asn Ala
                435                 440                 445

Asn Asn Ile Pro Glu Thr Ser Ile Asn Asn Tyr Lys Asn Val Pro Gly
                450                 455                 460

Ile Gly Phe Phe Asn Pro Gly Glu Arg Asp Ala Ile Ser Asn Asn Gly
465                 470                 475                 480

Gly Ser Ala Gly Gly Phe Ala Ala Gly Asn Thr Ala Ser Thr Ile Thr
                485                 490                 495

Val Ala Gly Ala Leu Leu Ala Ser Gly Gly Trp Asn Gly Asn Gly Thr
                500                 505                 510

Val Gln Ala Phe Leu Thr Pro Ser Gln Ser Ile Asn Tyr Val Glu Cys
                515                 520                 525

His Asp Ser Phe Thr Leu Asn Asp Ser Leu Trp Ser Ala Asp Pro Asn
530                 535                 540

Asp Ser Val Ala Thr His Gln Ala Arg Val Thr Leu Ala Asn Ala Thr
545                 550                 555                 560

Asn Ile Leu Ala Asn Gly Val Thr Phe Met Glu Thr Gly Gln Glu Phe
                565                 570                 575

Asp Gln Ser Lys Leu Val Asn Pro Ser Asn Leu Thr Pro Leu Ser Pro
                580                 585                 590

Thr Gln Thr Gln Ala Tyr Gln Ser Gly Ser Met Glu Lys Pro Ala Trp
                595                 600                 605

Tyr Pro Ala Ser Trp Asp Thr Ala Lys Asn Ser Tyr Asn Gly Leu Phe
                610                 615                 620

Gly Leu Ala Ser Asn Gly Thr Tyr Tyr Gly Asn Tyr Trp Pro Gly Ser
625                 630                 635                 640
```

```
Asn Leu Tyr Thr Pro Val Val Ala Gly Asp Val Val Asn Ala Met Asn
                645             650             655

Trp Asp Asn Val Lys Asp Asn Gln Asn Ala Val Asn Phe Ile Gly Asn
            660             665             670

Leu Met Lys Phe Lys Lys Ser Asn Pro Gln Phe Trp Pro Asp Asp Tyr
        675             680             685

Ser Lys Leu Ala Trp Thr Pro Thr Ser Ile Gly Val Glu Asn Val Thr
    690             695             700

Asn Ala Ser Asn Gly Val Ile Thr Glu Glu Leu Thr Ser Gly Ala Thr
705             710             715             720

Lys Tyr Leu Val Ile Leu Asn Ala Ser Gly Asn Ser Val Lys Ile Gly
            725             730             735

Gln Gly Gly Gln Phe Tyr Gly Val Ser Asn Leu Thr Gly Lys Thr Val
            740             745             750

Ile Ile Ser Asp Asp Ser Ser Leu Thr Ala Asn Gln Val Leu Asn Ser
        755             760             765

Ser Val Thr Leu Ser Asn Leu Thr Val Thr Val Ile Gln Leu Ser Lys
    770             775             780
```